(12) United States Patent
Tonkovich et al.

(10) Patent No.: US 9,856,447 B2
(45) Date of Patent: Jan. 2, 2018

(54) BIOREACTOR ARRAY AND METHODS OF COMBINATORIAL TESTING

(71) Applicant: HELIAE DEVELOPMENT LLC, Gilbert, AZ (US)

(72) Inventors: Anna Lee Tonkovich, Gilbert, AZ (US); Thomas Adame, Chandler, AZ (US); Shan Qin, Gilbert, AZ (US); Eneko Ganuza Taberna, Phoenix, AZ (US)

(73) Assignee: HELIAE DEVELOPMENT LLC, Gilbert, AZ (US)

( * ) Notice: Subject to any disclaimer, the term of this patent is extended or adjusted under 35 U.S.C. 154(b) by 23 days.

(21) Appl. No.: 14/805,267

(22) Filed: Jul. 21, 2015

(65) Prior Publication Data

US 2015/0322396 A1 Nov. 12, 2015

Related U.S. Application Data

(63) Continuation of application No. PCT/US2014/016462, filed on Feb. 14, 2014.

(60) Provisional application No. 61/850,623, filed on Feb. 19, 2013, provisional application No. 61/917,423, filed on Dec. 18, 2013.

(51) Int. Cl.
| | |
|---|---|
| *C12M 1/00* | (2006.01) |
| *C12M 3/00* | (2006.01) |
| *C12M 1/26* | (2006.01) |
| *C12M 1/34* | (2006.01) |
| *C12M 1/42* | (2006.01) |
| *C12M 1/02* | (2006.01) |
| *C12M 1/36* | (2006.01) |

(52) U.S. Cl.
CPC ............ *C12M 23/22* (2013.01); *C12M 21/02* (2013.01); *C12M 23/38* (2013.01); *C12M 23/44* (2013.01); *C12M 23/58* (2013.01); *C12M 29/00* (2013.01); *C12M 29/20* (2013.01); *C12M 33/00* (2013.01); *C12M 35/00* (2013.01); *C12M 41/00* (2013.01); *C12M 41/06* (2013.01); *C12M 41/12* (2013.01); *C12M 41/18* (2013.01); *C12M 41/26* (2013.01); *C12M 41/32* (2013.01); *C12M 41/34* (2013.01); *C12M 41/36* (2013.01); *C12M 41/48* (2013.01)

(58) Field of Classification Search
None
See application file for complete search history.

(56) References Cited

U.S. PATENT DOCUMENTS

| | | |
|---|---|---|
| 7,018,793 B1 | 3/2006 | Short |
| 8,102,518 B2 | 1/2012 | Haught |
| 8,268,553 B2 | 9/2012 | Mayfield |
| 8,507,253 B2 | 8/2013 | Berzin |
| 2005/0176584 A1 | 8/2005 | Kwak |
| 2009/0197322 A1 | 8/2009 | Goldman |
| 2012/0107921 A1 | 5/2012 | Willson |

FOREIGN PATENT DOCUMENTS

| | | | |
|---|---|---|---|
| CN | 101935610 | 1/2011 | |
| CN | 102286367 | 12/2011 | |
| WO | WO 2010/123848 A2 * | 10/2010 | ............... C12N 1/12 |
| WO | 2012071467 | 5/2012 | |

OTHER PUBLICATIONS

Wang et al., A Study on Inhibition of Ciliates by Acidified Alga Chlorella vulgaris Liquid, Chinese Library Classification (CLC) No. Q949.217, 2005.*
Rowley, Nitrogen and Phosphorus biomass-kinetic model for Chlorella Vulgaris in a Biofuel Production Scheme, Mar. 2010.*
Sampath-Wiley et al., A new filter that accurately mimics the solar UV-B specturm using standard UV lamps: the photochemical properties, stabilization and use of the urate anion liquid filter, Plant, Cell, and Environment (2011) 34, 261-269.*
Held et al, Screening for Optimal Algal Cell Growth and Neutral Lipid Production Conditions in Microplates. Accessed online Oct. 25, 2012 at: http://www.biotek.com/assets/tech_resources/SLAS2012_05_Algal_INAL_LF.pdf.
Chen, et al, Optical microplates for high-throughput screening of photosynthesis in lipid producing algae. Abstract Only. Lab Chip Oct. 21, 2012; 12 (20):3870-4.
Hernandez-Mireles et al. (27f) 96-Well Culture Microplates as a Microreactor Platform for Microalgae Research. Abstract Only. Presented at 2009 AIChE Annual Meeting in Nashville. TN Nov. 9, 2009, Accessed online Nov. 2, 2012 at: http://www3.aiche.org/proceedings/Abstract.aspx?PaperID+171118.
Jiraskova et al. High-Throughput Screening Technology for Monitoring Phytohormone Production in Microalgae. Abstract Only. Journal of Phycology, vol. 45, Issue 1, pp. 108-118, Feb. 2009.
Marques et al. Anchoring High-Throughput Screening Methods to Scale-UP Bioproduction of Siderophores. Process Biochemistry 47 (2012) 416-421.
Mertiti et al. Optical microplates for photonic high throughput screening og algal photosynthesis and biofuel production. ConF Proc IEEE Eng Med Biol Soc. 2011; 2011:482-5.
National Renewable Energy Laboratory. Algal Biofuels Research Laboratory. NREL/FS-5100-52195, Aug. 2011. Accessed online Oct. 22, 2012 at: http://www.nrel.gov/biomass/pdfs/52195.pdf.
Pereira et al. Microplate-based high throughput screening procedure for the isolation of lipi-rich marine microalgae. Biotechnology for Biofuels 2011, 4:61.

(Continued)

*Primary Examiner* — Suzanne M Noakes
*Assistant Examiner* — Stephen Chong
(74) *Attorney, Agent, or Firm* — Heliae Development LLC; Len Smith

(57) ABSTRACT

Methods and apparatus for culturing microorganisms are described, including culturing in mixotrophic culture conditions. A bioreactor array with multiple culture vessels with independently controllable inputs is used to culture similar cultures of microorganisms in which at least one parameter differs from other culture vessels in the bioreactor array.

12 Claims, No Drawings

(56) References Cited

OTHER PUBLICATIONS

Algenion. Phycomat 96-well twin layer microalgal cultivation technology. Brochure accessed online Oct. 25, 2012 at: http://www.algenion-biotec.de/downloads/phycomat_brochure_web_hires.pdf.
Pandey et al. Evaluation of Biomass Production of Spirulina maxima on Different Reported Media. Journal of Algal Biomass Utilization 2010, 1 (3): 70-81.
Infors HT. Sixfors The Multi-Minifermenter Brochure. Accessed Jan. 8, 2014.
Infors AG. Sixfors Operating Manual & User Guide. Accessed Jan. 8, 2014.
Cooksey et al. Fluorometric determination of the neutral lipid content of microalgal cells using Nile Red. Journal of Microbiological Methods, vol. 6, Issue 6, Sep. 1987, pp. 333-345.

\* cited by examiner

BIOREACTOR ARRAY AND METHODS OF COMBINATORIAL TESTING

CROSS REFERENCE TO RELATED APPLICATIONS

This application claims the benefit of PCT Application No. PCT/US2014/016462, filed Feb. 14, 2014, entitled Bioreactor Array and Methods of Combinatorial Testing, U.S. Provisional Application No. 61/850,623, filed Feb. 19, 2013, entitled Photobioreactor Array and Mixotrophic Culture, and U.S. Provisional Application No. 61/917,423, filed Dec. 18, 2013, entitled Photobioreactor Array and Mixotrophic Culture, the entire contents of which are hereby incorporated by reference.

BACKGROUND

Photosynthetic organisms have been cultured to produce chemicals and biologicals of interests such as fatty acids, proteins, hydrogen gas, pigments, carbohydrates, sugars, and vitamins for use in food, feed, pharmaceuticals, nutraceuticals, fuels, and other products.

Of particular interest in recent years has been the use of microorganisms, such as microalgae and photosynthetic bacteria cultures, themselves or extracts derived from the microorganism. A number of microalgal metabolites have commercial interest as chemical compounds and have been so produced. Many have attempted to grow microalgae, typically in open ponds, long tubes, and bags with tubes between them. Others have attempted growing microalgae in enclosed tank systems, but each type of system has encountered difficulties related to control and optimization of the microalgae culture. Heterotrophic microorganisms, such as microalgae and bacteria, have also been cultured in traditional stainless steel fermenters to produce for similar chemicals and biologicals for commercial products in the same fields.

In an attempt to enhance production of a microalgae culture, a parameter of the biocultivation process has been varied in an attempt to find the optimum range for that parameter.

However, it is known that multiple parameters interact with each other within a culture to give complex relationships regarding optimal ranges for each parameter. Even a simple component, such as the culture medium under auxotrophic conditions containing no more than salts, lacks simplistic optimization. For example, Pandey et al, Journal of Algal Biomass Utilization, 1(3) p. 70-81 (2010), reports very different yields using differing proportions of salts in their culturing medium even with all other culture parameters remaining unchanged. Within the article, it is noteworthy that no single salt concentration had an optimal range that controlled yield. Even different conventional culture media resulted in doubling the yield. The media compared were all previously published for *Spirulina* and previously optimized for *Spirulina* growth, yet when compared side-by-side, dramatically different yields resulted.

Given the potential market, the need for a large-scale microalgae growth system is evident; yet, the prior art systems have had little optimization before being built. Different bioreactors present different problems and are optimized differently around the parameters which are not changeable. Open ponds suffer from problems with contamination (e.g., organics, bacteria, fungi), changing conditions throughout the day and night (e.g., temperature, sunlight, wind), and other suboptimal cultivation conditions. Many bioreactors have difficulties with sufficient light reaching the microalgae for photosynthetic activity and in controlling the conditions (e.g., temperature, pH, nitrate levels). A system relying solely on ambient light as an energy source for the microalgae is susceptible to fluctuation with seasons and even clouds, which may vary random and non-reproducible manner making comparison between different runs difficult or impossible to interpret even when the same bioreactor is used.

Therefore, there is a need in the art for a system and method of optimizing culturing parameters to increase the efficiency of microalgae cultivation.

SUMMARY

The present invention provides a method and apparatus for cultivating microorganisms in a liquid or aqueous culture medium with control over the culturing parameters.

In one embodiment, a bioreactor array may comprise a plurality of culture vessels configured to contain an aqueous culture of microorganisms in an interior volume, each culturing vessel comprising an independently controllable: gas supply, nutrient supply, heat exchanger, harvesting mechanism, and light supply; at least one sensor configured to measure at least one culturing parameter of each culture vessel; and a programmable logic controller. In some embodiments the culture vessel may have a volume of 500 to 1000 ml. In some embodiments, the culture vessel may be transparent. In some embodiments, the culture vessel may comprise at least one opaque section.

In some embodiments, the gas supply may comprise at least one gas selected from the group consisting of: air, carbon dioxide, oxygen, and nitrogen. In some embodiments, the nutrient supply may comprise an organic carbon supply. In some embodiments, the harvesting system may comprise an overflow system configured to passively remove at least part of the aqueous culture volume at a culture volume less than a total volume of the culture vessel. In some embodiments, the at least one sensor may be selected from the group consisting of: pH sensor, temperature sensors, light sensors, dissolved oxygen sensors, dissolved carbon dioxide sensor, and optical density sensor. In some embodiments, the light supply may comprise a lighting device disposed outside of the culture vessel. In some embodiments, the light supply may comprise a lighting device disposed in the interior volume of the culture vessel.

In another embodiment, a method of culturing microorganisms may comprise providing culture of microorganisms in an aqueous culture medium in a plurality of culture vessels; independently controlling the supply to each culture vessel at least one from the group consisting of: light, at least one gas, at least one nutrient, and heat exchange; and wherein each culture vessel contains a culture of the same microorganisms cultured with different parameters selected from the group consisting of temperature, pH, amount of light, intensity of light, wavelengths of light, light photoperiod, light/dark cycle, concentrations of gases, and agitation from gas supply. In some embodiments, the at least one nutrient may comprise organic carbon.

In some embodiments, the method may further comprise harvesting at least part of the aqueous culture from the culture volume. In some embodiments, the different parameters may further comprise harvest rates. In some embodiments, the culture vessel may be supplied with light and organic carbon. In some embodiments, the culture may be supplied with organic carbon but no light.

In some embodiments, providing the culture of microorganisms in the aqueous culture medium in each culture vessel may comprise 0.5-1.5 grams of biomass. In some embodiments, providing the culture of microorganisms in the aqueous culture medium in each culture vessel comprises 500 to 1,000 ml of culture volume. In some embodiments, the method may further comprise monitoring the parameters of the culture of microorganisms in the plurality of culture vessels with at least one sensors and a programmable logic controller. In some embodiments, the supply of light may comprise at least two independently controllable light emitting diodes providing different wavelengths of light.

The current invention provides a method for strain conditioning, adaptation and selection. The method may be performed in a plurality of bioreactors where at least one parameter stressing the microorganism culture differs between bioreactors. Alternatively, the inventive reactors may be used to evaluate growth parameters or treatments (chemical or biological) to control or reduce contamination in microorganism cultures.

In another embodiments, the bioreactor array may comprise: a plurality of culture vessels configured to contain an aqueous culture of microorganisms in an interior volume, each culturing vessel comprising means for controlling the gas composition, nutrient composition, temperature, light exposure, and harvest of the aqueous culture of microorganisms; and means for measuring at least one culturing parameter of each culture vessel. In some embodiments, the bioreactor array may further comprise computer automated means for controlling at least one of the gas composition, nutrient composition, temperature, light exposure, and harvest of the aqueous culture of microorganisms in response to the at least one culturing parameters. In some embodiments the at least one culturing parameter may comprise at least one from the group consisting of: nutrient concentration, temperature, pH, amount of light, intensity of light, wavelengths of light, light photoperiod, light/dark cycle, concentrations of gases, and agitation from gas supply

DETAILED DESCRIPTION

While not wishing to be bound by any particularly theory, the present invention is believed to determine desirable effects on microorganisms, including photosynthetic microorganisms, and/or products as the result of the metabolism of microorganisms used.

For the purposes of this specification the term "photosynthetic microorganism" is intended to cover any phototrophic or mixotrophic or microorganism that is capable of utilizing light as a source of energy through photosynthesis. The photosynthesis need not be directly involved in producing the desired result. The photosynthesis need not even occur provided that an alternative energy source is provided. All organisms that utilize light for photosynthesis, of which phototrophic and mixotrophic species of microorganism are included.

The term "microorganism" refers to microscopic organisms such as microalgae and cyanobacteria. Microalgae include microscopic multi-cellular plants (e.g. duckweed), photosynthetic microorganisms, heterotrophic microorganisms, diatoms, dinoflagelattes, and unicellular algae.

The terms "microbiological culture", "microbial culture", or "microorganism culture" refer to a method or system for multiplying microorganisms through reproduction in a predetermined culture medium, including under controlled laboratory conditions. Microbiological cultures, microbial cultures, and microorganism cultures are used to multiply the organism, to determine the type of organism, or the abundance of the organism in the sample being tested. In liquid culture medium, the term microbiological, microbial, or microorganism culture generally refers to the entire liquid medium and the microorganisms in the liquid medium regardless of the vessel in which the culture resides. A liquid medium is often referred to as "media", "culture medium", or "culture media". The act of culturing is generally referred to as "culturing microorganisms" when emphasis is on plural microorganisms. The act of culturing is generally referred to as "culturing a microorganism" when importance is placed on a species or genus of microorganism. Microorganism culture is used synonymously with culture of microorganisms.

The terms "phototrophic", "phototrophy", "photoautotrophy", "photoautotrophic", and "autotroph" refer to culture conditions in which light and inorganic carbon (e.g., carbon dioxide, carbonate, bi-carbonate) may be applied to a culture of microorganisms. Microorganisms capable of growing in phototrophic conditions may use light as an energy source and inorganic carbon (e.g., carbon dioxide) as a carbon source. A microorganism in phototrophic conditions may produce oxygen.

The terms "mixotrophic" and "mixotrophy" refer to culture conditions in which light, organic carbon, and inorganic carbon (e.g., carbon dioxide, carbonate, bi-carbonate) may be applied to a culture of microorganisms. Microorganisms capable of growing in mixotrophic conditions have the metabolic profile of both phototrophic and heterotrophic microorganisms, and may use both light and organic carbon as energy sources, as well as both inorganic carbon and organic carbon as carbon sources. A mixotrophic microorganism may be using light, inorganic carbon, and organic carbon through the phototrophic and heterotrophic metabolisms simultaneously or may switch between the utilization of each metabolism. A microorganism in mixotrophic culture conditions may be a net oxygen or carbon dioxide producer depending on the energy source and carbon source utilized by the microorganism. Microorganisms capable of mixotrophic growth comprise microorganisms with the natural metabolism and ability to grow in mixotrophic conditions, as well as microorganisms which obtain the metabolism and ability through modification of cells by way of methods such as mutagenesis or genetic engineering.

The terms "heterotrophic" and "heterotrophy" refer to culture conditions in which organic carbon may be applied to a culture of microorganisms in the absence of light. Microorganisms capable of growing in heterotrophic conditions may use organic carbon as both an energy source and as a carbon source. A microorganism in heterotrophic conditions may produce carbon dioxide.

The organic carbon sources suitable for growing a microorganism mixotrophically may comprise: acetate, acetic acid, ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, sacchrose, partial or complete hydrolysates of starch, sucrose, tartaric, TCA-cycle organic acids, thin stillage, urea, industrial waste solutions, yeast extract, and combinations thereof. The organic carbon source may comprise any single source, combination of sources, and dilutions of single sources or combinations of sources.

Of particular use in the present invention are mixotrophic microorganisms such as, but not limited to *Agmenellum*,

*Amphora, Anabaena, Anacystis, Apistonema, Pleurochyrsis, Arthrospira (Spirulina), Botryococcus, Brachiomonas, Chlamydomonas, Chlorella, Chloroccum, Cruciplacolithus, Cylindrotheca, Coenochloris, Cyanophora, Cyclotella, Dunaliella, Emiliania, Euglena, Extubocellulus, Fragilaria, Galdieria, Goniotrichium, Haematococcus, Halochlorella, Isochyrsis, Leptocylindrus, Micractinium, Melosira, Monodus, Nostoc, Nannochloris, Nannochloropsis, Navicula, Neospongiococcum, Nitzschia., Odontella, Ochromonas, Ochrosphaera, Pavlova, Picochlorum, Phaeodactylum, Pleurochyrsis, Porphyridium, Poteriochromonas, Prymnesium, Rhodomonas, Scenedesmus, Skeletonema, Spumella, Stauroneis, Stichococcus, Auxenochlorella, Cheatoceros, Neochloris, Ocromonas, Porphiridium, Synechococcus, Synechocystis, Tetraselmis, Thraustochytrids, Thalassiosira*, and species thereof. Also included may be more unclassified new microalgal genera, species, or strains which may be poorly characterized or even newly discovered microorganisms. While certain high yielding strains are preferentially used, a considerable number of other organisms are known and under the property conditions may also produce biomass and various metabolites of interest. National Renewable Energy Laboratory (NREL) has selected 300 species of microalgae, both fresh water and salt water microalgae, including diatoms and green microalgae. Other organizations have large depositories of photosynthetic and non-photosynthetic microorganisms. Any of these and others may be used in the present invention. Known literature also describes a plurality of microorganisms capable of growth in phototrophic and heterotrophic culture conditions which is also of interest with this invention.

For the purposes of this specification the term "parameter" refers to any feature of the culturing of the microorganism or extraction or processing of the resulting culture. Examples may comprise: bioreactor design; microorganism strain selection; additional microorganism strain selection (if mixed culture); selection of media components and concentration of each; dissolved gases; gases in the atmosphere above the microorganism culture; carbon dioxide, oxygen and other gas amounts and pressures in the bioreactor; gas sparaging rate; gas bubble size; chemical carbon source (if any); content of, timing of and rate of addition of additional nutrients (e.g., organic carbon); fluid withdraw rate (i.e., harvesting rate); culture mixing rate; cell withdraw rate; initial cell concentration; maintenance of steady cell concentration; pH; salinity; osmotic pressure; temperature; amount of light; wavelength(s) of light; pulsing duration and rate of light; length of light and dark cycles; rate of increasing and decreasing light intensity during the lighting phase; selection of a chemical enhancing product production or its amount or timing of its addition; selection of chemical or physical inhibition of contaminating microorganisms (amount and timing also); manner of and rate of removal of wastes or contaminants; choice of added contaminant or proxy to mimic natural contamination; type of culture operation (e.g., batch, semi-batch, fed-batch, continuous); rate and timing for removal of secreted product(s); longevity of the culture; co-cultivation strategies and strain interactions; and timing of a change in one or more parameter in response to a set schedule or in response to a change in condition of one or more other condition.

The term "axenic" describes a culture of an organism that is entirely free of all other "contaminating" organisms (i.e., organisms that are detrimental to the health of the microalgae or cyanobacteria culture). Throughout the specification, axenic refers to a culture that when inoculated in an agar plate with bacterial basal medium, does not form any colonies other than the microorganism of interest. Axenic describes cultures not contaminated by or associated with any other living organisms such as but not limited to bacteria, cyanobacteria, microalgae and/or fungi. Axenic is usually used in reference to pure cultures of microorganisms that are completely free of the presence of other different organisms. An axenic culture of microalgae or cyanobacteria is completely free from other different organisms.

Should one seek to optimize multiple parameters, the combinations indicate one will generate a large set of test data of different culture parameters. This is particularly challenging for mixotrophic cultures with many additional complicating factors. This is impractical to attempt in a mass production system as it may take years of testing to optimize the parameters. Even then, because some of the apparatus and photosynthetic organisms drift over time, the comparison is far from perfect. By contrast, the present invention mimics mass production in a more manageable way which allows for easier evaluation of parameter combinations.

The present invention may isolate key parameters and mimic the conditions in a mass production system to allow optimization for different cultures of microorganisms. In mixotrophic culture the impact of light is less important than the contribution of growth energy and carbon from the organic carbon source. The units in the described invention are well mixed which allows for a volumetric reaction rate. For the mixotrophic reactions, growth is dominated by volumetric reactions rather than areal reactions resultant from solar input. Artificial light or solar light may be supplemental, and the majority of growth may be resultant from the organic carbon source.

Previous attempts to optimize parameters of a microorganism culture have relied upon rather simple lab scale selections which do not resemble real life situations, and thus the data produced does not translate to improved cultures in commercial production conditions. For example, traditionally, optimal microorganism strains are typically selected by growing different strains in multiwelled plates or separate small volume vessels and measuring the results of either cell growth or product production. These multiwelled plates are not well mixed and do not allow for a feedback mechanism with the consumption of carbon during the reaction given their small culture volume.

The control mechanisms for such a screening are different from those used in large scale production (i.e., commercial production). Further, this may not reflect actual results in mass production in a large bioreactor or even an open pond where parameters such as dissolved gases, depth of the culture, and lighting conditions vary dramatically from the screening system. The traditional selection using small volumes with poor mixing may not choose a desired optimal microorganism strain or culture parameters and may be more likely to select a strain optimized for a batch system resembling the selection system rather than any large scale continuous system.

During the operation of the array of vessels in the present invention, numerous sensors may be present with continuous monitoring of culture parameters. This allows for a thorough determination of preferred parameters. For example, one set of parameters may be ideal for the first few days which destroy the culture on, for example, day seven. Without constant monitoring, one would assume this set of parameters is unacceptable when looking only at the final result, however the set of parameter may be ideal provided that one make an adjustment on, for example, day five or harvest the culture before day seven.

Another embodiment of the present invention is the determination of the approximate cost and benefit of mass production using a photosynthetic microorganism in the bioreactor design stage before even building such a plant. Unlike conventional laboratory systems, the present invention mimics actual large scale production conditions, permitting extrapolation and translation of useful data.

While considerable work has been conducted on phototrophic microalgae including the optimization of parameters for growth, no systems are commercially available to rapidly test mixotrophic cultures of microalgae in parallel for rapid combinatorial screening of strains, process conditions, media, growth factors, organic carbon source, contamination vectors, and more. The number of parameters affecting growth and photosynthetic microorganism longevity are greater in mixotrophic systems than for phototrophic systems with the inclusion of the complexity of non-light energy sources, such as an organic carbon source, and the ensuing challenges of contamination (e.g., bacteria, fungi, ciliates) that may feed on the organic carbon source.

The apparatus used in the present invention may be fitted with a wide selection of sensors. Preferred sensors may comprise: pH, temperature, dissolved oxygen (DO), dissolved carbon dioxide, cell density, concentrations of various chemicals in the medium, amount of light, and wavelengths of light received. A sample of culture medium may be withdrawn for testing or the testing may be done on or inside the culture vessel itself. One example of a continuous flowing sensor of numerous components in water is exemplified by U.S. Pat. No. 8,102,518.

The apparatus may be operated in an axenic mode or may be operated in a non-axenic mode. An advantage to a non-axenic mode is the understanding of the impact of growth conditions on bacteria both in terms of proliferation and individual strains of bacteria. The apparatus may be used to test the response in microalgae and contaminants to treatments applied for increasing microalgae growth, longevity, or reduce contaminants.

While every individual vessel may have its own set of sensors, it may be beneficial to have a single common sensor for each type of parameter. For example, by having a line to collect exhaust gases from each vessel separately, the same sensor can provide repeated sequential measurements from each gas stream. Likewise, for withdrawing a small sample of liquid and running it by a single sensor for each type of parameter before returning the sample to culture vessel. This avoids any difficulty or drift in separate sensors.

The light may be provided to the cultures by any conventional lighting source such as fluorescent bulbs, light emitting diodes (LEDs), ambient room light, sunlight, etc. In some embodiments, the light source may be a lighting device exterior to the vessel. Reflected, refracted and filtered light may also be used. In some embodiments, light may be provided to the culture from inside the culture vessels by a submerged light source such as fiber optics, LEDs or an LED strip or other lighting device disposed within the interior volume of the culture vessel. Controlling lighting parameters such as the intensity, amount, duration, pulsing, light/dark cycle, wavelengths provided, etc., are particularly desirable and these parameters may desirably change during the culturing process and in response to other changing parameters.

In one embodiment, light may be only applied to a portion of the vessel to evaluate the impact of reduced light, no light, high light, or partial light on the growth and productivity of the target microorganisms as well as unwanted species (i.e., contamination).

These and other parameters that are harmful to the photosynthetic microorganism may be used if desired to enhance product production or the desirability of it. For example, at the end of the culture cycle, one may wish to dramatically increase the amount of light to photobleach (i.e., stress) the microorganism to aid in recovery of a product by autolysis or separation of the product.

The types of products that can be produced include, whole cells, extracts, lipids, proteins, pigments, hormones, polysaccharides, and others. The amounts and proportions of each are frequently altered by altering the process parameters. The product may be an action also such as degradation of wastes or catalytic biotransformation of one chemical to another.

Changing parameters during cultivation to have a desirable effect on the photosynthetic microorganism's metabolism may be preferred. While laboratory experimental examples are known of adding a chemical to enhance or stop production or growth, they are not typically done under conditions suitable for mass production due to a lack of understanding of the interactions and effects. The present invention would allow for a systematic evaluation of interactions through combinatorial testing and reduce risk for introducing chemicals or treatments at a mass cultivation scale.

Supplies of gases to the culture vessels of the present invention may be provided by a common line from a common reservoir. Individual valves and meters may adjust one or more gasses before being optionally mixed together and supplied to the cultures. A bubbler or sparger at or near the bottom of the culture vessels may be used to deliver the gases and provide mixing in the culture. Laminar flow of bubbles may be used to provide mixing for shear sensitive microorganisms. If desired, mixing baffles or a separate active mixer of any conventional type may be added.

During the culturing, addition of any chemical and/or withdraw (and optional recycle) of culture medium (with photosynthetic microorganisms) may be performed as a parameter. The culture may be run in batch, fed batch, semi continuous or fully continuous methods.

A further embodiment is the use of a fed-batch mode of operation whereby the organic carbon source may be slowly fed as the organisms grow. The organic carbon source may be used to control pH or may be added sparingly to disfavor the competitive production of by-products, which may include bacteria or other unwanted microalgae species. The organic carbon source may be concentrated or dilute. The volume of the culture increases with the addition of the organic carbon source. In some embodiments, the culture may be periodically harvested or continuously harvested with an overflow port that controls the volume to a preset level. The use of the parallel culturing vessels may be used to concurrently test the different modes of harvest as a parameter that affects growth and longevity.

While exemplified by a clear vessel, the vessel may comprise translucent or even opaque regions in part or in its entirety, with at least one source for delivering light or feature allowing light to be delivered. For example, it may be desirable to have steel supporting structures in contact with the vessel or to have the vessel in contact with a metal heat sink for heating or cooling the vessel (i.e., heat exchange), either of which may block light from reaching the culture volume.

While the cultures are discussed as producing a product, the culture may also be used to degrade or remove undesirable substances from the culture medium. This would be especially desirable for optimizing the culture parameters to degrade wastewater or thrive on waste mediums. The culture may also react with or catalytically transform one feedstock into a more desired product during either growth or steady state conditions in light or dark.

Some or all of the bioreactor vessels may be sealed which allows for pressurization and prevents outside contamination from entering the vessel.

After each batch or periodically if continuous, the bioreactor may be easily disassembled for ease of cleaning. The array of vessels in the bioreactor may be individually removable for cleaning, analysis, product recovery, or medium addition.

The present invention may also incorporate the use of disposable or recyclable components that may comprise the use of a plastic bag to serve as the reaction vessel. A bag reaction vessel may be disposed after conducting a desired experiment. The bag may be supported by a structure for frame to maintain the distance from the culture volume to the light source.

For the purposes of this specification the term "clear" refers to transparent or translucent to light, particularly allowing the transmission of the light wavelengths utilized for photosynthesis by the photosynthetic microorganism. It is understood that even "clear" vessels will have some light transmission loss that may range from about 1 to 40%. The desirable wavelengths, such as photosynthetically active radiation (PAR) light or light promoting production of a product, may vary somewhat between different species of photosynthetic microalgae. A "clear" material may be opaque or hinder other wavelengths of visible light and other wavelengths of electromagnetic radiation. A "clear" material is clear only in the sense of its optical properties and only to an adequate degree for allowing light to pass through to the photosynthetic microorganism.

In another embodiment of the present invention, the light source may emit only certain wavelengths of light that have value in promoting growth or production of desired product. LEDs of a specific wavelength or wavelength enhanced LEDs emitting light in the desired wavelengths may be used. The light source need not exclusively emit desired wavelengths (e.g., PAR light) but rather may be enriched for desired wavelengths in this embodiment of the invention. A number of different electro luminescence devices known per se may be used.

Also, an optical filter may be added between the light source and the photosynthetic microorganism to block harmful wavelengths or wavelengths which reduce production of the desired product(s). Harmful wavelengths may even degrade the desired product(s) or degrade an intermediate in the metabolic pathway of the desired product(s). Certain harmful wavelengths may not be harmful to the photosynthetic microorganism but rather encourage a different metabolism away from maximum production of the desired product(s). The optical filter may be a device, thin film, particle, or simple compound, which reflects or adsorbs some of the undesired wavelengths or even neutral wavelengths. This filter may be outside or inside a culture vessel.

Nutrients required by the photosynthetic microorganism, e.g. sodium nitrate and sodium phosphate or others, may be added manually either in the solid form by premeasured manual addition or may be added manually or automatically as a premeasured diluted solution in water via the top of the vessel or elsewhere in a line. These nutrients may also be added with the organic carbon media, which may be added continuously or semi-continuously in response to changing parameters, such as pH or volume and the like. The nutrients may be pure ingredients, known mixtures or relatively raw materials such as the wastewater from a food processing facility. All added products to the system are preferably sterile to limit the amount of contamination introduced into the culture vessel. The addition of $CO_2$ creates carbonic acid in water that will lower the pH during the cycle time of a batch, therefore the pH may be constantly monitored (by testing a sample or by a pH sensor located in the vessel or a line of circulating liquid) and a buffer or an alkaline material, such as sodium hydroxide or sodium bicarbonate etc., may be added via the same technique as the nutrients to control the pH at the desired level for optimum organism growth and performance. When the bioreactor is open vented, there may be no pressure other than the liquid head pressure in the vessel and the vessel may be run at or close to the full volume level. The top of the vessel may be used for adding nutrients, mounting pH instrumentation, adding control chemicals, and periodic internal cleanout of the reaction vessel and lines. Likewise for a closed bioreactor, the top may also be used for the same features provided that they are sealed with the vessel top.

A feature of the present invention is to have common reservoirs of materials to add to the multiple culture vessels. They may use a common line with manifolds and individual or group valves or adjustable meters to deliver the same or differing amounts to different vessels. This provides further control of the amounts and concentrations added to different test vessels thereby providing better comparisons when one or more parameters are changed.

Another feature may be to have automated control of the various parameters based on preset programs or feedback loops from the sensors. Since many slightly different cultures of photosynthetic microorganisms may be present, it may be impractical to monitor all of them separately.

Additionally, data may be collected for storage and comparison analysis. Having as many of the parameters controlled along with common data collection makes for a better comparison. In the present invention, a simple run of the bioreactor apparatus may provide a considerable amount of comparable data for data mining by conventional statistical analysis such as the statistical programs from SAS Institute Inc. (100 SAS Campus Drive, Cary, N.C. 27513-2414).

The concentrations of the nutrient and pH control solutions are carefully selected to minimize damaging or killing the microorganisms, and to provide long term control during the growth and product maturation phases (e.g., oil accumulation, pigment accumulation) of the process. Redundant pH probes may be included to provide easy switchover to a new probe when the recording probe fails to operate. It is noted that a system that filters the microorganisms and provides clean water to the pH probes could extend the life of the probes in this service.

Contamination by undesired microorganisms may be reduced by adding an inhibitory gas, such as ozone, chlorine dioxide, ethylene oxide etc., in the headspace or by the $CO_2$ sparger or a separate gas sparger. If a specific contaminant is of particular concern, an antibiotic, which may be less harmful to the desired photosynthetic organism, may be added to the culture medium. Likewise, the culture conditions may be modified to inhibit the contaminant without excessive harm to the photosynthetic microorganism.

A preferred embodiment of the present invention is a bioreactor design for changing conditions while culturing photosynthetic microorganisms. The bioreactor allows for a batch of microalgae or other microorganism to undergo several days of both continuous growth and an oil (or other metabolite) buildup phase of production in batch or semi-batch conditions. Alternatively, continuous production may be used. The culture conditions may alternate between enhancing growth of the photosynthetic microorganism and enhancing production of a metabolite, such as a fatty acid or other desired compound(s). The culture may also be designed to degrade unwanted or harmful compounds in the medium.

The area outside the culture vessel may use an air ventilation system to remove the heat produced by the light bulbs and other equipment.

Computer controlled adjustable motors and valves may be responsive to the culturing process conditions. Preset parameters and changes in parameters may be effected by computer control, by feedback loop, or manually by an operator. Redundant manual or override controls may be present. Specific operations may comprise: the addition of pH control agents, gases, liquids, nutrients; removal of culture liquid or gases; adjusting the agitation, recirculation, and gas introduction rates; and temperature control. The operation may be run continuously and indefinitely to study the long-term effects or to test for and optimize microorganism longevity.

At the end of a cycle, or continuously, when microorganisms are removed from the system, the desired product(s) may be extracted from the microorganism in a separate downstream process such as, but not limited to, solvent extraction, supercritical fluid extraction, and cell disruption. The method of extraction and recovery will depend on the particular product(s) targeted, and are preferably done by a manner known per se.

Example 1: The Bioreactor Array

A set of identical 1 liter glass culture vessels having a working culture volume of 500-800 ml and columns with dimensions of 4.57 cm inside diameter (ID)×5.1 cm outside diameter (OD)×61.0 cm height (H) (1.8" ID×2.0" OD×24" H). A rubber stopper is pressed into the open top of the column to serve as a lid. Holes were cut into the rubber stopper to accommodate a 0.762 OD×66.04 cm (0.3" OD×26" H) glass capillary tube for aeration, a 0.601 cm OD×30.48 cm H (0.24" OD×12" H) pH probe (other designs employed a shorter pH probe (12 mm×152 mm)), a sample/fill port via 0.476 cm OD×0.159 cm ID Tygon tubing (3/16" OD×1/16 ID), an organic carbon liquid (e.g., acetic acid) injection via 0.3 cm OD×0.1 cm ID Tygon tubing (0.117" OD×0.039" ID), a thermistor 0.0635 cm OD×3.81 cm L@30.48 cm depth (0.25" OD×1.5" L@12" depth), and a 0.254 cm (0.1") hole for venting. The probes were placed at a position to be submerged into the culture medium contained in the glass culture vessels. A 24V DC peristaltic pump rated at 1 ml/min flow was used to pump organic carbon liquid to the columns. A 0-10 kΩ potentiometer was used to control the peristaltic pump speed. The pump was actuated using a signal from a Hanna pH controller (these controllers have a hysteresis of 0.1). A 50 ml polypropylene centrifuge tube was used as the acetic acid reservoir. Aeration was controlled via a rotameter (0.7 L/min maximum flow). A Luer Lock was placed on the end of the sample/fill Tygon tubing. Lighting was provided via an 8 bulb T5 fluorescent bulb light fixture. The fluorescent bulbs apply light from about 50 to 500 microeinsteins/m$^2$ s. The axes of the light tubes were aligned perpendicular to the vertical axis of the each culture vessel for this specific unit. Alternatively, the lights can be aligned parallel to the vertical axis of each culture vessel. A box fan was placed adjacent to the lights blowing toward the columns to help remove some of the heat from the lights. Data logging is accomplished by way of a C-RIO and NI software Initially there were no controls for the $CO_2$; it was fed at a slow constant rate (app. 0.02 LPM). An optional water bath type cooling system made of a 2 ft by 2 ft (61 cm by 61 cm) flat panel made of clear acrylic was used as the bath. A submersible pump was placed into an insulated reservoir and pumped water through a 2400 btu/h chiller on its way to the water bath. From the water bath water flowed back to the reservoir. The water bath system is able to hold temperatures to 20° C. (no heating capability).

Additional Bioreactor Array Embodiments

An alternative system may mount each culture vessel on an aluminum block with a Peltier temperature control system, which is independently variable instead of a water bath.

Another bioreactor array design may comprise multiple variations. LED lights may be added in place of the fluorescent lights and use multiple diodes (e.g., red, far red, blue) with wavelengths that range from about 300 to about 800 nm. Each diode may be dimmed and variably controlled independent of one another. A second modification may be a set of overflow ports placed at 600, 700, and 800 ml on each 1000 ml column. An overflow reservoir may be added and plumbed to the desired overflow ports. The unused ports may be capped.

In another bioreactor array embodiment, the water bath cooling system may be replaced by thermoelectric cooling. The column stand for this system may be fully enclosed with two clear plexiglass faces in front and back for viewing and lighting the columns. The top, bottom, and sides may be constructed from 0.75 inch (2 cm) plywood to help insulate the chamber. The chamber may be split down the center with 0.75 inch (2 cm) plywood creating two chambers that house 4 column reactors and 4 acid reservoirs per chamber. Thermoelectric coolers (app. 80-100 btu/h) may be added to each chamber and controlled via simple thermostat. LED lights may be employed in place of the fluorescent lights. These lights may have multiple diodes (e.g., red, blue, and white diodes) that may independently controlled as for intensity, photoperiod, and other parameters. A variable voltage power supply may be used to power the liquid delivery pumps. This allows the pumps to be sped up or slowed down easily with no need for resistors. Rotameters may be added and plumbed into the sparger air to facilitate the use of an additional gas.

Example 2: Control of the Bioreactor Array

The bioreactor array system of Example 1 was fitted with a programmable logic controller (PLC) controls/data logging system. The PLC is used to control temperature, pH, dissolved oxygen (DO), light intensity/spectrum, light cycle, and growth mode (phototrophic, heterotrophic, mixotrophic) all of which can be manipulated through a user friendly touch screen mounted directly to the unit. This system uses Peltier devices for heating/cooling, which can be used for climate control or can be mounted to the column directly for individual temperature control. Controls for $CO_2$ as well as acid or alkali injection for pH control are used. There are multiple versions of harvest systems that can be employed on this system (e.g., manual, overflow, pumped) depending on operator choice. An inert gas can be added to sparger gas to help control DO via a feed back control loop between a DO probe and solenoid to control gas flow. A continuous media addition system can be added for concentration control and are driven by a signal from an optical density type sensor. Media and acid consumption are monitored by load sensors installed on the reservoirs.

Example 3: Bioreactor Array Operation

The column bioreactor array system of Example 1 is used to determine whether an antimicrobial gas treatment can prevent or treat cultures that were contaminated. A single *Chlorella* sp. strain is added to all vessels along with conventional BG-11 growth medium at a concentration of 1 g/l. A harmful contaminant *Polyarthra vulgaris*, is added to each culture vessel at the designated time shown in Table 1. Various concentrations of antimicrobial gases (i.e., ozone, chlorine dioxide, ethylene oxide) are mixed with carbon dioxide enriched air and bubbled through the culture vessels. The array of vessels are grown for a 10 day cycle under 12 hours light/12 hours darkness for 5 days using nutrient-sufficient medium (growth phase) followed by 5 days without a nitrogen source in the medium (oil accumulation phase). The conditions and all other parameters are held constant with a common light source and common lines delivering the same amounts of solids, liquids and gases to each. The combinations of culture treatments are given in Table 1.

TABLE 1

| Culture vessel number | Gas treatment | Gas concentration | Time of adding contaminant |
|---|---|---|---|
| 1 (control) | None | None | Initial |
| 2 (control) | None | None | 3 days |
| 3 (control) | None | None | 8 days |
| 4 | Ozone | Low | Initial |
| 5 | Ozone | Low | 3 days |
| 6 | Ozone | Low | 8 days |
| 7 | Ozone | Intermediate | Initial |
| 8 | Ozone | Intermediate | 3 days |
| 9 | Ozone | Intermediate | 8 days |
| 10 | Ozone | High | Initial |
| 11 | Ozone | High | 3 days |
| 12 | Ozone | High | 8 days |
| 13 | Chlorine dioxide | Low | Initial |
| 14 | Chlorine dioxide | Low | 3 days |
| 15 | Chlorine dioxide | Low | 8 days |
| 16 | Chlorine dioxide | Intermediate | Initial |
| 17 | Chlorine dioxide | Intermediate | 3 days |
| 18 | Chlorine dioxide | Intermediate | 8 days |
| 19 | Chlorine dioxide | High | Initial |
| 20 | Chlorine dioxide | High | 3 days |
| 21 | Chlorine dioxide | High | 8 days |
| 22 | Ethylene oxide | Low | Initial |
| 23 | Ethylene oxide | Low | 3 days |
| 24 | Ethylene oxide | Low | 8 days |
| 25 | Ethylene oxide | Intermediate | Initial |
| 26 | Ethylene oxide | Intermediate | 3 days |
| 27 | Ethylene oxide | Intermediate | 8 days |
| 28 | Ethylene oxide | High | Initial |
| 29 | Ethylene oxide | High | 3 days |
| 30 | Ethylene oxide | High | 8 days |
| 31 | Ozone | Low | None |
| 32 | Ozone | Intermediate | None |
| 33 | Ozone | High | None |
| 34 | Chlorine dioxide | Low | None |
| 35 | Chlorine dioxide | Intermediate | None |
| 36 | Chlorine dioxide | High | None |
| 37 | Ethylene oxide | Low | None |
| 38 | Ethylene oxide | Intermediate | None |
| 39 | Ethylene oxide | High | None |
| 40 (control) | None | None | None |

The differing gas treatments without adding a contaminant serve as a control for determining the baseline of inhibitory effects of the gas on the microalgae. Likewise the differing time for inoculation with the contaminant serve to determine a baseline of the harmful effects on the culture depending on the growth cycle. The differing gasses and their differing concentrations serve as techniques being optimized between the harmful effects on the microalgae and the beneficial harmful effects on the contaminating microbe.

At the end of the 10 day cycle the resulting culture liquid is centrifuged and dried, the biomass weighed, the protein content estimated by the Comassie Blue method and the lipid content estimated by the Nile Red method (Cooksey et al, (1987)). The entire process can be completed in two weeks as compared to a year or more using a single system with the potential for changing conditions (especially light conditions) and instrument drift during that time.

The method may be repeated with any combination of photosynthetic microorganisms and contaminant and may be repeated where the antimicrobial gas is not added until after the contaminant has been added and is detectably affecting the cell growth. This approach may determine whether any antimicrobial gas treatment can rescue a contaminated culture. Further methods may be run with other combinations of microorganisms and varied parameters to draw other conclusions in a similar manner and short time frame.

Previous systems using the 2 ft (61 cm) by 2 ft (61 cm) flat panel reactors with a volume of 10-15 L required about 15 g of biomass to inoculate each reactor. Combinatorial experiments using eight reactors would require about 120 g of biomass and about 120 L of prepared media. In one embodiment of bioreactor array system, the culture vessel may have an operating volume of 500 to 1000 ml, which requires only 0.5-1.5 g, or about 1 g, of biomass to inoculate each reactor. Combinatorial experiments using eight culture vessels of the instant invention would require about 8 g of biomass and about 4-8 L of prepared media. The dramatic reduction in biomass and culture media resources required allows for more experiments to be done, but still produces the minimum amount of biomass required for composition analytical tests to be performed. The results from the composition analytical tests may be used for product development and verification of parameters for larger scale bioreactors.

The capability for each culturing vessel in the bioreactor array to be have individual and independently controllable organic carbon, lighting, and gas supply systems provides the flexibility to operate in phototrophic, mixotrophic, and heterotrophic culturing conditions. In some embodiments, the culturing vessel may receive light and air or carbon dioxide gas, but no organic carbon to operate in phototrophic culture conditions. In some embodiments, the culturing vessel may receive light, organic carbon, and gases (e.g., air, carbon dioxide, oxygen) to operate in mixotrophic culture conditions. In some embodiments, the culturing vessel may receive organic carbon and oxygen or air, but no light to operate in heterotrophic conditions. Parameters may be independently controlled in the bioreactor array as described through the specification to produce biomass and combinatorial testing results in any of the described culture conditions. Dissolved oxygen (DO) control becomes important in mixotrophic and heterotrophic conditions due to the consumption of oxygen by the microorganisms and high cell densities that may result from rapid growth. An inert gas may be added to the sparger air to help control the dissolved oxygen via a DO probe and a solenoid to control gas flow.

Multiple available harvest systems may comprise a manual harvest system, an overflow harvested system set a desired volume (e.g., 600 ml, 700 ml, 800 ml), or a pumped harvest system. The harvest systems may be controlled for different harvesting rates from the different culture vessels by methods such as, but not limited to: controlling the harvesting pump devices at different settings, and setting the overflow volume level at different volume levels in different culture vessels. Continuous media addition may be added for cell concentration control independently of the harvest system or in combination with the harvest system, and may be driven by a signal from an optical density sensor.

In one embodiment the bioreactor array may comprise a plurality of culture vessels configured to contain an aqueous culture of microorganisms in an interior volume of the culture vessel. Each culture vessel in the bioreactor array may comprise an independently controlled supply of gas, nutrients, and light. The gases may comprise air, oxygen, carbon dioxide, nitrogen, and/or other inert gases. The supply of gases may be controlled to maintain levels of dissolved carbon dioxide, dissolved oxygen, pH, and mixing by aeration. The supply may be controlled as to the type of gas, volume of gas, concentration of gas, flow rate, and bubble size. The nutrients may comprise minerals in an aqueous medium and/or an organic carbon source. The light may be supplied by lighting devices disposed outside the culture vessel, within the interior volume of the culture vessel, or combinations thereof. The independently controlled light supply may be completely turned off for heterotrophic culture conditions, or varied in amount, intensity, photoperiod, light/dark cycle, and wavelength of light for phototrophic and mixotrophic culture conditions. In some embodiments, the lighting device may comprise at least two light emitting diodes (LEDs) that provide different wavelengths of light and are independently controllable.

In some embodiments, each culture vessel may further comprise an independently controllable heat exchanger to control temperature of the culture. In some embodiments, the culture vessel may be translucent, transparent or clear, which facilitates the use of a lighting device disposed outside of the culture vessel. In some embodiments, the culture vessel comprises at least one opaque section which blocks light exterior to the culture vessel. A culture vessel with at least one opaque section may reduce light for mixotrophic conditions, block all light for heterotrophic conditions, or facilitate the use of a lighting device disposed within the interior volume of the culture vessel.

In some embodiments, the bioreactor array may further comprise an independently controlled harvesting system for each culture vessel. Multiple available harvest systems may comprise a manual harvest system, an overflow harvested system set a desired volume (e.g., 600 ml, 700 ml, 800 ml), or a pumped harvest system. The harvest systems may be controlled for different harvesting rates from the different culture vessels by methods such as, but not limited to: controlling the harvesting pump devices at different settings, and setting the overflow volume level at different volume levels in different culture vessels. Continuous media addition may be added for concentration control independently of the harvest system or in combination with the harvest system, and may be driven by a signal from an optical density sensor.

In some embodiments, the bioreactor array further comprises at least one sensor configured to measure at least one culturing parameter of each culture vessel. The at least one sensor may be selected from the group consisting of: pH sensor, temperature sensors, light sensors, dissolved oxygen sensors, dissolved carbon dioxide sensor, and optical density sensor. Sensors at each culturing vessel may be coordinated for control of the other features of the bioreactor array through a programmable logic controller, and for data recording through a data logging device.

Embodiments of the bioreactor array may be used in methods of culturing microorganisms, particularly for combinatorial testing of different parameters for cultures of the same microorganisms, the same parameters for cultures of different microorganisms, and combinations thereof. In one embodiment, a method comprises providing a culture of microorganisms in an aqueous culture medium in a plurality of culture vessels; independently controlling the supply of at least one selected from the group consisting of light, at least one gas, at least one nutrient, and heat exchange to each culture vessel; and wherein each culture vessel contains a culture of the same microorganisms with different parameters. The parameters may be selected from the group consisting of temperature, pH, amount of light, intensity of light, wavelengths of light, light photoperiod, light/dark cycle, concentration of gases, and agitation from gas supply. For embodiments with harvesting systems, the harvesting rate may also be an independently controlled parameter for each culture vessel.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto. All patents and references cited herein are explicitly incorporated by reference in their entirety.

What is claimed is:

1. A method for conducting combinatorial testing of microorganisms, comprising:
    a. providing a plurality of cultures comprising a composition of 0.5-1.5 grams of microalgae capable of using organic carbon as an energy and carbon source in a volume of 500-1,000 ml of an aqueous culture medium and a population of contaminating microorganisms consisting of at least one selected from the group consisting of bacteria, fungi, and ciliates, in a plurality of closed culture vessels comprising lids;
    b. independently controlling the supply to each culture vessel of at least one from the group consisting of:
        i. light;
        ii. at least one gas; and
        iii. heat exchange;
    c. supplying acetic acid to the plurality of cultures in response to a detected culture pH, wherein the acetic acid provides a source of organic carbon for utilization as energy and carbon by the microalgae and controls the culture pH;
    d. venting gas through the lids of the culturing vessels; and
    e. testing combinations of different parameters in parallel to determine the effect on the microalgae and the population of contaminating microorganisms, wherein each culture vessel contains a culture of the same composition cultured with different combinations of parameters selected from the group consisting of culture temperature, culture pH, amount of light, intensity of light, wavelengths of light, light photoperiod, light/dark cycle, rate of organic carbon supply, concentrations of gases, and agitation from gas supply.

2. The method of claim 1, further comprising harvesting at least part of the composition from the culture volume, and wherein the different parameters further comprise harvest rates.

3. The method of claim 1, further comprising continuously monitoring the parameters of the culture of the microalgae and the population of contaminating microorganisms in the plurality of culture vessels with at least one sensor and a programmable logic controller.

4. The method of claim 1, wherein the parameters are adjusting during the testing.

5. The method of claim 1, wherein the testing is conducted in mixotrophic culture conditions.

6. The method of claim 1, wherein the testing is conducted in heterotrophic culture conditions.

7. The method of claim 1, further comprising controlling the supply of light by blocking select wavelengths of light with an optical filter.

8. The method of claim 1, wherein the at least one gas comprises an inhibitory gas selected from the group consisting of ozone, chlorine dioxide, and ethylene oxide, and the inhibitory gas reduces the population of contaminating microorganisms in the culture.

9. The method of claim 2, wherein the amount of microalgae harvested from a single culture initially comprising 0.5-1.5 grams of the microalgae in 500-1,000 ml of the aqueous culture medium is at least enough biomass to perform composition analytical tests on the microalgae.

10. The method of claim 3, wherein the step of independently controlling the supply of at least one gas to each culturing vessel further comprises sparging air into each culture vessel and controlling an addition of an inert gas into the sparged air by using a dissolved oxygen sensor and the programmable logic controller.

11. The method of claim 1, further comprising mixing the cultures with the supply of at least one gas and at least one from the group consisting of a baffle and a separate active mixer.

12. The method of claim 1, wherein the parameters tested further comprise recycling of the culture medium.

* * * * *